United States Patent [19]

Heinrich et al.

[11] Patent Number: 4,973,352

[45] Date of Patent: Nov. 27, 1990

[54] HERBICIDAL AGENTS IN THE FORM OF AQUEOUS TRANSPARENT MICROEMULSIONS

[75] Inventors: Rudolf Heinrich; Konrad Albrecht, both of Kelkheim; Hans Schumacher, Flörsheim am Main, all of Fed. Rep. of Germany

[73] Assignee: Hoechst Aktiengesellschaft, Frankfurt am Main, Fed. Rep. of Germany

[21] Appl. No.: 315,390

[22] Filed: Feb. 24, 1989

[30] Foreign Application Priority Data

Feb. 27, 1988 [DE] Fed. Rep. of Germany ....... 3806294

[51] Int. Cl.$^5$ ............................................. A01N 43/02
[52] U.S. Cl. ........................................... 71/91; 71/88; 71/DIG. 1; 71/90; 71/92; 71/94
[58] Field of Search ................ 71/88, 91, DIG. 1, 90, 71/92, 94

[56] References Cited

U.S. PATENT DOCUMENTS

| | | | |
|---|---|---|---|
| 3,954,442 | 5/1976 | Becker et al. | 71/108 |
| 4,125,398 | 11/1978 | Roth | 71/DIG. 1 |
| 4,130,413 | 12/1978 | Handte et al. | 71/88 |
| 4,238,626 | 12/1980 | Helmut Nahm | 71/108 |
| 4,336,057 | 6/1982 | Bieringer et al. | 71/88 |
| 4,448,602 | 5/1984 | Schumacher | 71/88 |
| 4,500,348 | 2/1985 | Hausmann et al. | 71/103 |

FOREIGN PATENT DOCUMENTS

| | | |
|---|---|---|
| 1227353 | 4/1981 | Canada . |
| 0047396 | 4/1981 | European Pat. Off. . |
| 0118759 | 8/1984 | European Pat. Off. . |
| 2136828 | 7/1971 | Fed. Rep. of Germany . |
| 2223894 | 12/1973 | Fed. Rep. of Germany . |
| 2640730 | 10/1976 | Fed. Rep. of Germany . |
| 3111934 | 3/1981 | Fed. Rep. of Germany . |
| 1599121 | 7/1977 | United Kingdom . |
| 2042539 | 2/1980 | United Kingdom . |
| 2082914A | 3/1982 | United Kingdom . |
| 2115285 | 2/1983 | United Kingdom . |

OTHER PUBLICATIONS

The Pesticide Manual, 8, Auflage, pp. 63 to 64.

*Primary Examiner*—Glennon H. Hollrah
*Assistant Examiner*—Eric J. Kraus
*Attorney, Agent, or Firm*—Curtis, Morris & Safford

[57] ABSTRACT

Herbicidal aqueous microemulsions containing a combination of a herbicidal phenoxyphenoxy- or hetercaryloxyphenoxy-carboxylic acid ester with a salt of the herbicide bentazone (3-isopropyl-1H-benzo-2,1,3-thiadiazin-4-one 2,2-dioxide) as active substances; one or more emulsifiers wetting agents from among calcium dodecylbenzenesulfonate, ethoxylated castor oil, the ethoxylated nonylphenols, the alkanol polyglycol ethers or the fatty acid polyglycol esters, and one or more organic solvents from among the aromatics or ketones, are storage-stable at low and higher temperatures and show no inhomogeneities.

11 Claims, No Drawings

HERBICIDAL AGENTS IN THE FORM OF AQUEOUS TRANSPARENT MICROEMULSIONS

DESCRIPTION

The invention relates to herbicidal agents in the form of concentrated microemulsions which contain a phenoxyphenoxycarboxylic acid ester or a heteroaryloxyphenoxycarboxylic acid ester and a salt of the active substance bentazone (=3-isopropyl-1H-benzo-2,1,3-thiadiazin-4-one 2,2-dioxide) as herbicidal active substances.

It is known and described in EP-A 118,759 (CA-1,227,353) that solutions of phenoxyphenoxycarboxylic acids and derivatives thereof in aromatic solvents can be formulated with the aid of terminally phosphorylated ethylene oxide/ propylene oxide/ethylene oxide block copolymers in aqueous phase to give milky-white concentrated emulsions.

"The Pesticide Manual", 8th edition, pp. 63 and 64 furthermore describes that bentazone in the form of its salts can be combined with the salts of MCPA, MCPB, dichlorprop or CMPP as an aqueous formulation (SL). Suspension concentrates of bentazone with dichlorprop and isoproturon or of bentazone with atrazine and also emulsifiable concentrates of bentazone with propanil or wettable powder formulations of bentazone with cyanazine and dichlorprop are also mentioned.

However, stable formulations of bentazone salts with a phenoxy- (or heteroaryl)phenoxycarboxylic acid ester, such as diclofop-methyl or fenoxaprop-ethyl, could not be prepared hitherto. These active substances are combined by known processes in the manner that, shortly prior to the application of the bentazone, appropriate proportions of emulsifiable concentrate of the combination partner are added to the slurry. However, this process is complicated, time-consuming and can easily result in misdosages in practice.

The object therefore arose to combine an aqueous solution of a bentazone salt with a solution of a phenoxy- (or heteroaryloxy)phenoxycarboxylic acid ester in an organic solvent in a single formulation. The difficulty in achieving this object was to formulate the aqueous solutions of the bentazone salts, which have a high specific gravity ($d_{20} \geq 1.24$ g/ml), with the virtually water-insoluble carboxylic acid esters which are only dissolved in organic solvents ($d_{20} \leq 1$ g/ml) as a homogeneous, physically and chemically stable formulation, with the prevention of phase separation or any type of coagulation.

It became evident that the terminally phosphorylated ethylene oxide/propylene oxide/ethylene oxide block copolymers described in EP-A 118,759 (CA 1,227,353) and the water-soluble dispersers of the type of the phosphorylated alkylaryl polyethylene oxide, described in EP-A 47,396 (GB-A 2,082,914), did not lead to the desired result when the procedure described therein was followed. The products obtained with these emulsifiers were milky to slightly translucent, and phase separation occurred after already a hours.

Similar problems were observed on the phosphorylated polystyrylphenyl polyethylene oxides described in EP-A 33,291. Furthermore, only colloidal emulsions were obtained using the alkylaryl polyglycol ether compounds described in DE-A 3,111,934 (US-A 4,500,348).

Surprisingly, it was now found that transparent microemulsions can be prepared when selected emulsifiers are used together with the abovementioned active substances, which microemulsions remain physically and chemically stable and do not show inhomogeneities even after fairly long storage both in the cold and at higher temperatures.

The present invention thus relates to herbicidal agents on the basis of aqueous concentrated microemulsions, containing (a) a herbicidal phenoxyphenoxy- or heteroaryloxyphenoxycarboxylic acid ester and a salt of the herbicide bentazone (3-isopropyl-1H-benzo-2,1,3-thiadiazin-4-one 2,2-dioxide) as active substances, (b) one or more emulsifiers or wetting agents from amongst calcium dodecylbenzenesulfonate, ethoxylated castor oil, the ethoxylated nonylphenols, the alkanol polyglycol ethers or the fatty acid polyglycol esters, (c) one or more organic solvents from amongst the aromatics or ketones and (d) water.

Bentazone salts which are employed according to the invention are, in particular, the alkali (Na, K) ammonium or alkylammonium salts.

As herbicidal phenoxy (or heteroaryloxy)-phenoxycarboxylic acid esters, the known substituted phenoxyphenoxy-, quinoxalyloxyphenoxy-, pyridyloxyphenoxy-, benzoxazolyloxyphenoxy- or benzothiazolyloxyphenoxycarboxylic acid esters are employed in the form of the pure optical isomers or as isomer mixtures (for example racemates). The compounds are described in, for example, DE-A 2,136,828, (US-A 4,238,626); DE-A 2,223,894, (US-A 3,954,442); British Patent 2,042,539; British Patent 1,599,121; DE-A 2,640,730 (US-A 4,130,413). The ($C_1$-$C_4$)alkyl esters, ($C_2$-$C_4$)-alkenyl esters or ($C_3$-$C_4$)alkynyl esters are particularly suitable.

Amongst these herbicides, the following active substances may be mentioned in particular:
methyl 2-(4-(2,4-dichlorophenoxy)phenoxy)propionate (diclofop-methyl),
methyl 2-(4-(4-bromo-2-chlorophenoxy)phenoxy)propionate,
methyl 2-(4-(4-trifluoromethylphenoxy)phenoxy)propionate,
methyl 2-(4-(2-chloro-4-trifluoromethylphenoxy)-phenoxy)propionate,
ethyl 4-(4-(4-trifluoromethylphenoxy)phenoxy)pent-2-enoate,
ethyl 2-(4-(3,5-dichloropyridyl-2-oxy)phenoxy)propionate,
methyl or 2-ethoxyethyl 2-(4-(3-chloro-5-trifluoromethylpyridyl-2-oxy)phenoxypropionate (haloxyfop-methyl or haloxyfop-2-ethoxyethyl),
propargyl 2-(4-(3,5-dichloropyridyl-2-oxy)phenoxy)-propionate,
ethyl 2-(4-(6-chlorobenzoxazol-2-yloxy)phenoxy)propionate (fenoxaprop-ethyl),
ethyl 2-(4-(6-chlorobenzothiazol-2-yloxy)phenoxy)propionate (fenthiaprop-ethyl),
methyl 2-(4-(3-chloro-5-trifluoromethyl-2-pyridyloxy)-phenoxy)propionate,
butyl 2-(4-(5-trifluoromethyl-2-pyridyloxy)phenoxypropionate (fluazifop-butyl),
ethyl 2-(4-(6-chloro-2-quinoxalyloxy)-phenoxypropionate (quizalofop-ethyl) and
ethyl 2-(4-(6-fluoro-2-quinoxalyloxy)phenoxy)propionate.

According to the invention, the active substances diclofop-methyl and fenoxaprop-ethyl are particularly important here. Most of the abovementioned active substances are described in "The Pesticide Manual", 8th edition 1987, British Crop Protection Council.

Ethoxylated castor oil, which is to be used according to the invention, contains in particular 20 to 60 EO units (EO=ethylene oxide). Examples of products which can be employed are ®Emulsogen 400 or ®Emulsogen 360 (manufactured by Hoechst AG). The ethoxylated nonylphenols contain 20–200 EO. These include, for example, ®Arkopal N 100 (manufactured by Hoechst AG). Alkanol polyglycol ethers which are preferably mentioned are ethoxylated ($C_8$–$C_{20}$)alkanols having an EO content of 3 to 20 EO, for example ®Genapol X 060 (manufactured by Hoechst AG). The fatty acid polyglycyol ester particularly contain 12–18 Carbon atoms in the fatty acid moiety. Of the emulsifiers mentioned, the most suitable according to the invention are ethoxylated castor oil and the alkanol polyglycol ethers.

Moreover, small amounts (up to 10 %) of other customary anionic or non-ionic emulsifiers or wetting agents, for example Na salts of alkyl biglycol ether sulfate, can be added to the formulations according to the invention without considerably changing the properties of the formulations.

Examples of suitable aromatic solvents are toluene, xylenes, higher-boiling fractions of aromatics, methylnaphthalenes, and, as ketones, in particular cyclohexanone.

The plant-protection agent combinations according to the invention contain a total proportion of active substance of 5–50 % by weight, preferably 20–35 % by weight; furthermore 5–40 % by weight; preferably 10–25 % by weight, of solvent; 10–30 % by weight, preferably 15–25 % by weight, of emulsifiers or wetting agents, and 20–70 % by weight, preferably 30–50 % by weight, of water, which is required for dissolving the bentazone salts.

In the formulations, the aqueous phase:organic phase ratio can vary between 10:1 and 2:1. In general, the active substance concentration in the aqueous phase is between 20 to 70 % by weight, in the organic phase between 1 and 80 % by weight. The upper limit is determined in each case by the solubility of the active substance used.

The invention furthermore relates to a process for the preparation of the agents according to the invention. For this purpose, the required amounts of the abovementioned components are transferred to a zone of high turbulence at temperatures between 10° and 60° C., advantageously at room temperature or slightly above, until the stable, transparent microemulsion desired has formed.

For carrying out the process in practice, the aqueous phase is prepared first from the solution of the bentazone salt, the wetting agent and, if appropriate, additional water. The water-insoluble active substance to be emulsified is then dissolved in the organic solvent, and the emulsifier is added. The organic phase thus formed is then allowed to flow slowly and with vigorous stirring into the aqueous phase. After some time, a transparent microemulsion is formed from the initially milky macroemulsion.

If appropriate, dispersing can also be carried out by a shaking operation or a static mixer, and is advantageously continued until the preparation is homogeneous in itself. Advantageously, the dispersing operation is carried out at room temperature, but it can also be effected in the cold or at higher temperatures.

The examples which follow are taken to illustrate the present invention in greater detail.

FORMULATION EXAMPLES

EXAMPLE 1

10 % by weight of a fatty alcohol polyglycol ether (having 8 EO) are added to 54 % by weight of an aqueous solution of the Na salt of bentazone (53 % strength), and the mixture is stirred until the wetting agent has formed a clear solution. 3 % by weight of fenthiaprop-ethyl are dissolved in 10 % by weight of a mixture of aromatic (boiling range 219° C.–282° C.) and 3 % by weight of cyclohexanone, and 10 % by weight of fatty acid polyglycol ester (having 40 EO) and 10 % by weight of a fatty alcohol polyglycol ether (having 6 EO) are added, and the mixture is stirred briefly until free of streaks. This organic phase is then added slowly with vigorous stirring to the aqueous phase. After a short time, a transparent microemulsion is formed from the initially milky emulsion. The emulsion is chemically stable and stable on use.

EXAMPLE 2

6 % by weight of a fatty alcohol polyglycol ether (having 8 EO) in 24 % by weight of water are added to 42 % by weight of 53 % strength aqueous solution of a Na salt of bentazone, stirring is effected as in Example 1. 2.2 % by weight of fenoxaprop-ethyl are dissolved in 8 % by weight of an aromatic mixture (219° C.–282° C.), and 10 % by weight of fatty acid polyglycol ester (having 40 EO) and 5.8 % by weight of calcium dodecylbenzenesulfonate are added, and the mixture is stirred briefly. The organic phase is then added as indicated in Example 1, and the procedure indicated in Example 1 is followed. The preparation is chemically stable and stable on use.

EXAMPLE 3

35 % by weight of an aqueous solution of the dimethylammonium salt of bentazone are stirred with 10 % by weight of water as indicated in Example 1.

5 % by weight of diclofop-methyl are dissolved in 17 % by weight of xylene and 5 % by weight of cyclohexanone, and 14 % by weight of a fatty acid polyglycol ester and 14 % by weight of calcium dodecylbenzenesulfonate are added, and the mixture is stirred briefly. The organic phase is then added as indicated in Example 1, and the procedure indicated in Example 1 is followed. The preparation is chemically stable and stable on use.

EXAMPLE 4

24 % by weight of water are added to 42 % by weight of a 53 % strength aqueous solution of Na salt of bentazone, and the mixture is stirred as in Example 1. 2.2 % by weight of fenoxaprop-ethyl are dissolved in 10 % by weight of an aromatic mixture (219°–282° C.), and 10 % by weight of fatty acid polyglycol ester (having 40 EO) and 11.8 % by weight of a fatty alcohol polyglycol ether (having 6 EO) are added, and the mixture is stirred briefly. The organic phase is then added as in Example 1, and the procedure indicated in Example 1 is followed. The preparation is chemically stable and stable on use.

We claim:

1. A herbicidal agent on the basis of aqueous concentrated transparent microemulsions, containing
   (a) 20 to 35% by weight of an active substance mixture of a phenoxyphenoxy- to heteroaryloxyphenoxycarboxylic acid ester and a salt of the herbicide bentazone,
   (b) 15 to 30% by weight of one or more emulsifiers or wetting agents selected from the group consisting of calcium dodecylbenzenesulfonate, ethoxylated castor oil having 20 to 60 EO, ethoxylated nonylphenols having 20 to 200 EO, alkanol polyglycol ethers having 3 to 20 EO and fatty acid polyglycol esters having 12 to 18 C-atoms in the fatty acid moiety,
   (c) 5 to 25% by weight of organic solvents selected from the group consisting of aromatics and ketones, and
   (d) 20 to 50% by weight of water.

2. A herbicidal agent as claimed in claim 1, containing as the phenoxyphenoxy- or heteroaryloxyphenoxycarboxylic acid ester, an active substance from amongst
   methyl 2-(4-(2,4-dichlorophenoxy)phenoxy)propionate (diclofop-methyl),
   methyl 2-(4-(4-bromo-2-chlorophenoxy)phenoxy)propionate,
   methyl 2-(4-(4-trifluoromethylphenoxy)phenoxy)propionate,
   methyl 2-(4-(2-chloro-4-trifluoromethylphenoxy)phenoxy)propionate,
   ethyl 4-(4-(4-trifluoromethylphenoxy)phenoxy)pent-2-enoate,
   ethyl 2-(4-(3,5-dichloropyridyl-2-oxy)phenoxy)propionate,
   methyl or 2-ethoxyethyl 2-(4-(3-chloro-5-trifluoromethylpyridyl-2-oxy)phenoxypropionate (haloxyfop-methyl or haloxyfop-2-ethoxyethyl),
   propargyl 2-(4-(3,5-dichloropyridyl-2-oxy)phenoxy)propionate,
   ethyl 2-(4-(6-chlorobenzoxazol-2-yloxy)phenoxy)propionate (fenoxaprop-ethyl),
   ethyl 2-(4-(6-chlorobenzothiazol-2-yloxy)phenoxy)propionate (fenthiaprop-ethyl),
   methyl 2-(4-(3-chloro-5-trifluoromethyl-2-pyridyloxy)phenoxy)propionate,
   butyl 2-(4-(5-trifluoromethyl-2-pyridyloxy)phenoxypropionate (fluazifop-butyl),
   ethyl 2-(4-(6-chloro-2-quinoxalyloxy)-phenoxypropionate (quizalofop-ethyl) and
   ethyl 2-(4-(6-fluoro-2-quinoxalyloxy)phenoxy)propionate, either as pure optical isomers or as mixtures thereof.

3. A herbicidal agent as claimed in claim 2, containing, as emulsifiers, ethoxylated castor oil having 20–60 EO or ethoxylated ($C_8$–$C_{20}$) alkanols having 3–20 EO.

4. A herbicidal agent as claimed in claim 1, containing, as emulsifiers, ethoxylated castor oil having 20–60 EO or ethoxylated ($C_8$–$C_{20}$)alkanols having 3–20 EO.

5. A herbicidal agent as claimed in claim 4, wherein the active substance mixture comprises diclofop-methyl or fenoxaprop-ethyl and the sodium salt of bentazone.

6. A herbicidal agent as claimed in claim 1, containing 2 to 5% by weight of a phenoxyphenoxy- or heteroaryloxyphenoxycarboxylic acid ester and 18 to 30% by weight of the sodium, potassium, ammonium or alkylammonium salt of bentazone.

7. A herbicidal agent as claimed in claim 6, wherein the active substance mixture comprises diclofopmethyl or fenoxaprop-ethyl and the sodium salt of bentazone.

8. A herbicidal agent as claimed in claim 7, wherein the emulsifiers or wetting agents are selected from the group consisting of calcium dodecylbenzenesulfonate, alkanol polyglycol ethers having 3 to 20 EO and fatty acid polyglycol esters having 12 to 18 C-atoms in the fatty acid moiety.

9. A herbicidal agent as claimed in claim 1, containing 20 to 35% by weight of an active substance mixture of fenoxaprop-ethyl and the sodium salt of bentazone, 15 to 30% by weight of a fatty alcohol polyglycol ether having 3–20 EO, 5 to 25% by weight of higher boiling aromatic solvents and 20 to 50% by weight of water.

10. A method for controlling undesirable plants which comprises applying to an undesirable plant or soil or a cultivated area in which said plant grows or may grow an effective amount of a herbicidal agent on the basis of aqueous concentrated transparent microemulsions, containing
    (a) 20 to 35% by weight of an active substance mixture of a phenoxyphenoxy- or heteroaryloxyphenoxycarboxylic acid ester and a salt of the herbicide bentazone,
    (b) 15 to 30% by weight of one or more emulsifiers or wetting agents selected from the group consisting of calcium dodecylbenzenesulfonate, ethoxylated castor oil having 20 to 60 EO, ethoxylated nonylphenols having 20 to 200 EO, alkanol polyglycol ethers having 3 to 20 EO and fatty acid polyglycol esters having 12 to 18 C-atoms in the fatty acid moiety,
    (c) 5 to 25% by weight of organic solvents selected from the group consisting of aromatics and ketones, and
    (d) 20 to 50% by weight of water.

11. A method as claimed in claim 10, wherein said undesirable plants are controlled in crops.

* * * * *